United States Patent [19]
Barth et al.

[11] Patent Number: 5,702,293
[45] Date of Patent: Dec. 30, 1997

[54] HOLDING FIXTURE FOR METALLOGRAPHIC MOUNT POLISHING

[75] Inventors: Clyde H. Barth, Ballston Lake; Charles E. Cramer, Schenectady, both of N.Y.

[73] Assignee: The United States of America as represented by the United States Department of Energy, Washington, D.C.

[21] Appl. No.: 740,513

[22] Filed: Oct. 30, 1996

[51] Int. Cl.$^6$ ............................................. B24B 41/06
[52] U.S. Cl. ........................ 451/364; 451/285; 451/365
[58] Field of Search ........................... 451/364, 365, 451/389, 390, 41, 287, 314, 320, 321, 323, 272, 278, 285, 286, 406

[56] References Cited

U.S. PATENT DOCUMENTS 2,095,503  10/1937  Keenan ........................ 451/285
3,763,611  10/1973  Duhring et al. ................ 451/364

FOREIGN PATENT DOCUMENTS 660736  11/1951  United Kingdom ............... 451/364

*Primary Examiner*—Robert A. Rose
*Assistant Examiner*—George Nguyen
*Attorney, Agent, or Firm*—John T. Lucas; William R. Moser; Paul A. Gottlieb

[57] ABSTRACT

A fixture for holding mounted specimens for polishing, having an arm; a body attached to one end of the arm, the body having at least one flange having an opening to accommodate a mounted specimen; and a means applying pressure against the outer surface of the mounted specimen to hold the specimen in contact with the polishing surface.

6 Claims, 3 Drawing Sheets

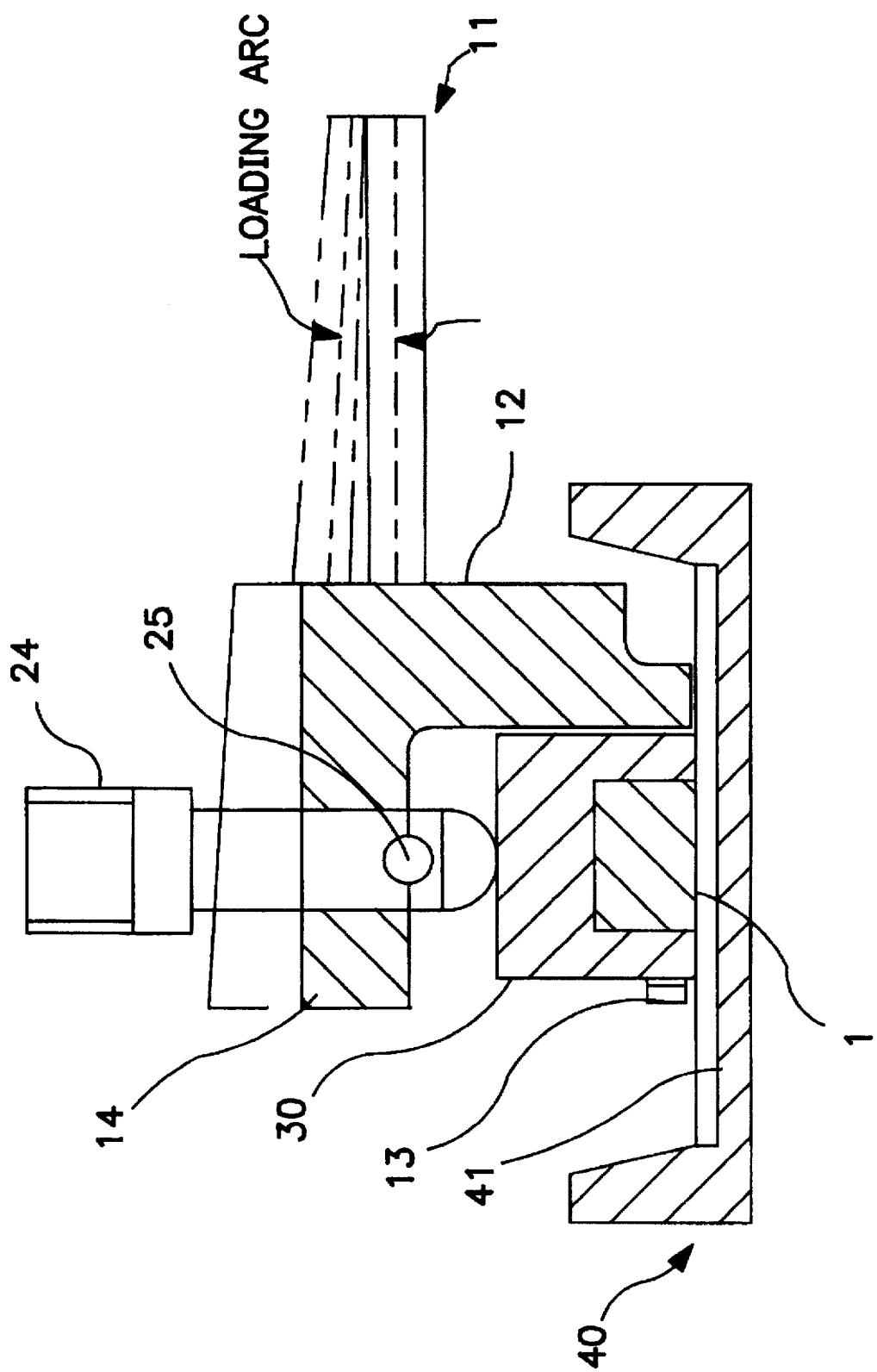

HOLDING FIXTURE FOR METALLOGRAPHIC MOUNT POLISHING

FIELD OF THE INVENTION

The present invention relates to fixturing for holding mounted metallic specimens for polishing, with particular usefulness in preparing radioactive specimens for metallographic examination.

BACKGROUND OF THE INVENTION

Preparation for metallographic examination of radioactive specimens requires two basic steps: (1) mounting, which involves embedding a specimen in a plastic medium for ease of manipulation; and (2) mount surface preparation, which involves processing (e.g. polishing) a surface of the specimen to reveal specific metallurgical features.

The second step, mount surface preparation, typically consists of a series of coarse to fine grinding steps, followed by polishing steps that use polishing compounds and fast attack chemicals. Fast attack chemicals are highly corrosive solutions that in application, are designed to remove smeared metal remaining from previous polishing steps. These chemicals, however, are also highly corrosive to other metals, including the polishing equipment itself. Therefore, the equipment must be cleaned after each use by disassembling and flushing completely with water.

When radioactive specimens are involved, a remote manipulator must be used to clean the equipment. As a result, cleaning is awkward and liberal use of water is prohibited. Consequently, the equipment is often inadequately cleaned, resulting in corrosion that causes equipment failure. Corrosion is especially severe in the larger, conventional equipment designed to accommodate several mounted specimens ("mounts") simultaneously. The large diameter rotating platter used to hold abrasive material or polishing compound in contact with counter-rotating mounts disperses the fast attack chemicals away from the mounted specimen over a large area of the equipment, resulting in a large surface area of the equipment that is subject to corrosion.

One attempt in the prior art toward solving these problems was to use smaller, less complicated equipment that would minimize the surface area upon which the fast attack chemicals are dispersed. A smaller polishing machine, the "Minimet", manufactured by Buehler, Ltd., was designed to process the surface of a mounted specimen by polishing it on a stationary cloth contained within a stationary, small diameter non-corrosive cup, typically a plastic cup approximately three inches in diameter. Because the cup small, non-moving, and non-corrosive, and because with the Minimet only the mounted specimen moves, action is more precisely controlled and chemical waste is minimized and dispersed.

Unfortunately, the Minimet requires that the specimens be mounted in a particular way, creating additional waste and partially destroying the specimen. Referring to FIG. 1, the conventional fixturing configuration required that a 3/16-inch diameter hole 6 be drilled through the center of the back of the mounting material 2 surrounding the specimen 1 (collectively referred to as mount 30 in FIGS. 2 and 3), to within ¼-inch of the face of the specimen. A load arm 3 then needed to be inserted into the hole, coupling the mount to the machine motion at a point below the center of gravity to prevent tipping.

This drilling into the specimen is undesirable, however, because it generates radioactive waste, creating cleanup and material accountability problems. Moreover, drilling damages the specimens for any subsequent remounting to view other surfaces.

It is therefore an object of the present invention to provide a fixture for holding mounted specimens for processing in smaller polishing equipment, such as the Minimet, without drilling into the body of the specimen or otherwise damaging the specimen's structural integrity.

It is a further object of the present invention to provide a fixture for holding mounted specimens that is easily handled by a remote manipulator and is capable of thorough cleaning with relative ease.

Another object of the present invention is to provide a holding fixture that applies the proper load pressure point and lateral support to yield a mount prepared surface that is polished and acceptably flat.

SUMMARY OF THE INVENTION

The holding fixture of the present invention comprises an arm, having a main body or chassis attached to one end. The other end couples to and becomes an extension of the polishing machine motion. The chassis has at least two flanges, with the first flange having an opening of sufficient dimensions (e.g. diameter) to allow insertion of the mounted specimen. The first flange is thick enough so that the wall of the opening is correspondingly tall enough to hold the specimen stable and in place. The second flange has an opening, axially parallel to the opening in the first flange, into which is inserted a means for applying pressure against the outer surface of the mounted specimen to hold the specimen in contact with the polishing surface. Sufficient distance must exist between the first and second flanges to allow access to horizontally insert the mount.

An advantage of the holding fixture of the present invention is that it eliminates the need for drilling holes into or otherwise physically damaging the specimen.

Another advantage of the holding fixture of the present invention is that it is easily manipulated by a remote manipulator. Mounts can be easily inserted and removed without altering the holding fixture.

Yet another advantage of the holding fixture of the present invention is that it is easy to thoroughly clean after use, and thus less subject to build-up of corrosive residues.

Yet another advantage of the holding fixture of the present invention is that it yields polished flat mounts regardless of the height of the mount.

BRIEF DESCRIPTION OF THE DRAWINGS

FIG. 3 is a cutaway side view of the holding fixture of the present invention assembled and holding a mounted specimen in contact with a polishing surface.

DETAILED DESCRIPTION OF THE PREFERRED EMBODIMENT

Figure 1:
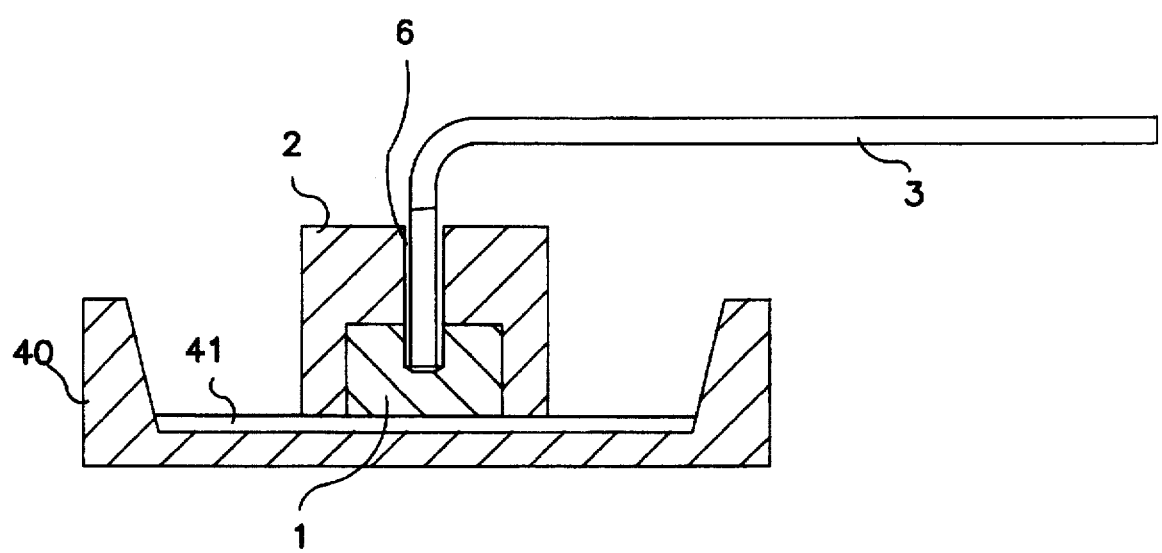
FIG. 1 is a cutaway side view depicting conventional fixturing for processing a mounted specimen in smaller machinery.
Figure 2:
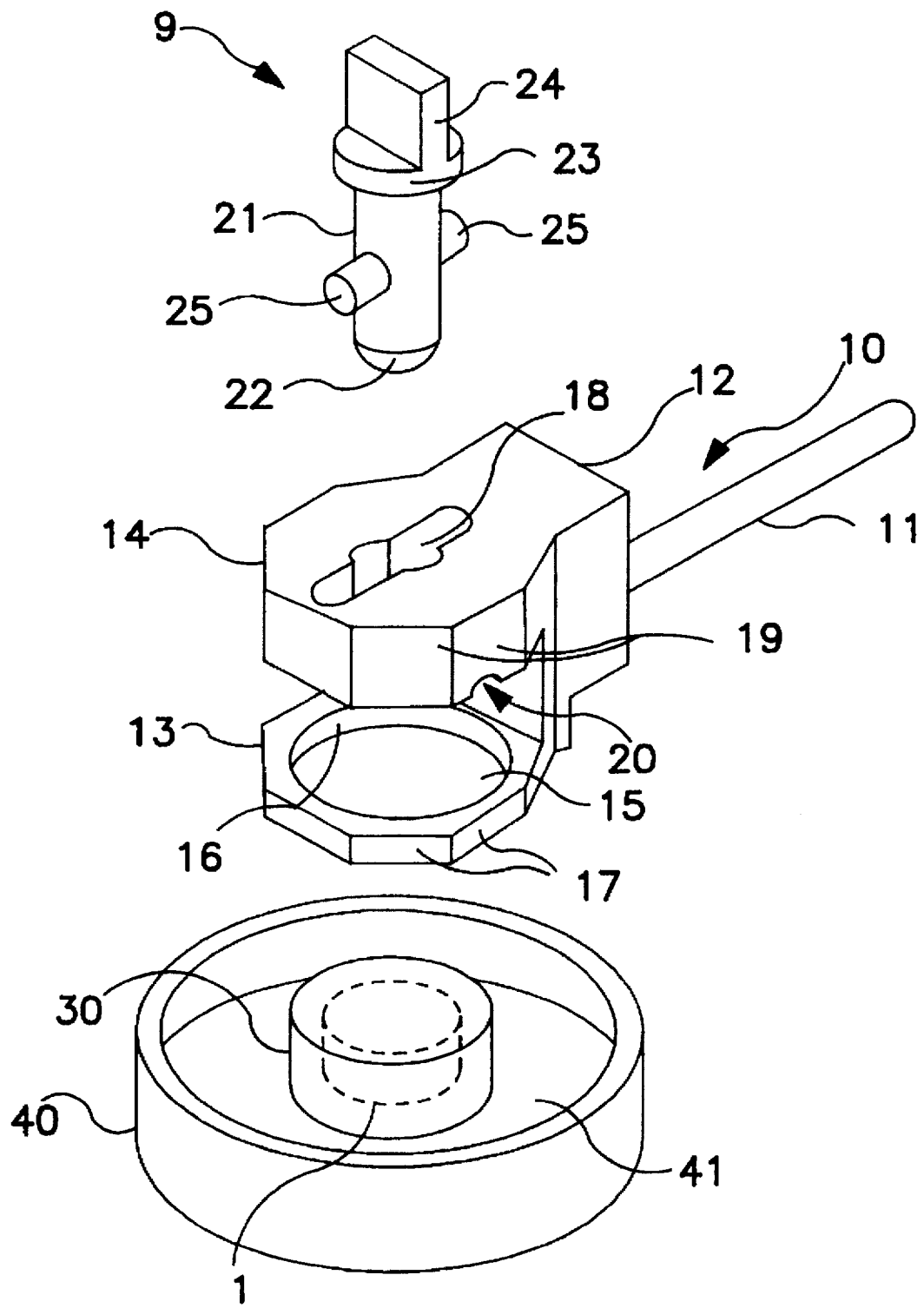
FIG. 2 is an isometric, exploded view of the holding fixture of the present invention.

Referring to FIG. 2, the preferred embodiment of the holding fixture of the present invention comprises two basic components: a locking pressure mechanism 9 and a chassis 10. Both components are preferably constructed of a strong, non-corrosive material, such as Delrin™ or other acetal resin, thermoplastic polymers.

Structurally, locking pressure mechanism 9 comprises a cylindrical body 21 with a rounded end 22. The rounded end assures point contact between the pressure point and center of the back of the mount, thus off-center contact caused in instances where the back of the mount has an irregular surface and is not flat or parallel to the mount face; and where the loading arc as shown in FIG. 3 changes as the mount thickness decreases during polishing. Were off-center contact to occur, the result would be a polished mount face that would be slightly convex and unacceptable. At the other end of the cylindrical body 21 is head 23 with perpendicular flange 24 protruding from the top surface of head 23 opposite the cylindrical body 21. The configuration of head 23 and the perpendicular flange 24 allows for secure connection to the polishing equipment. Flange 24 is the surface that is grasped by a remote manipulator and is the handling surface which is used to insert the pressure point. Head 23 has both a top and bottom surface. The top surface is used to resist the downward force applied by the manipulator fingers in the insertion operation. The bottom surface limits the insert distance into flange 14. Attached to the cylindrical body 21 and axially perpendicular thereto are two locking posts 25.

Arm 11 is an attachment shaft, preferably constructed from stainless steel or other non-corrosive material, that couples the chassis 10 to the polishing machine's rotary reciprocating motion. The arm 11 also transmits the downward force delivered by the polishing machine to the chassis and through pressure mechanism 9. The downward force in conjunction with the rotary motion applied to the mount back surface causes the polishing action to the mount face. Chassis 10 is comprised of a body 12 having two flanges 13 and 14. Flange 13 should be thick enough such that the wall 16 of opening 15 will support a sufficient surface area of mount 30 to hold the mount stable and in place. Flange 13 provides lateral support to the mount at a point below the mount's center of gravity. This assures that circular and reciprocating motion from the polishing equipment is transferred to the mount near the mount face, rather than higher up on the mount, to prevent tipping and thus maintain a square, flat polished face. The clearance between the mount 30 and the wall 16 should be large enough that the mount is easily inserted and afforded enough space to self-align between the locking pressure mechanism 9 and the polishing surface The second flange 14 is preferably parallel to flange 13 and has an opening 18 to accommodate insertion of the locking pressure mechanism 9. Opening 15 of flange 13 and opening 18 of flange 14 should be axially parallel, and preferably should be aligned. Having the axes aligned allows the locking pressure mechanism 9 to apply pressure at the center of the back of mount 30. Flange 14 has notches 20 spatially placed apart to correspond with the locking posts 25 of locking pressure mechanism 9.

Chassis 10 is preferably constructed having flanges with open space between them, rather that being constructed as one solid body with an opening bored therein to accommodate the mount. This open construction reduces the risk of incomplete cleaning. The open space results in less internal, concealed surface area that might be missed during cleaning and might collect residue of the fast attack chemicals. The open space also allows for insertion of the mount from either side rather that being limited to the bottom only.

Referring to FIGS. 2 and 3, chassis 10 is placed over mount 30 so that the mount is inserted through opening 15. Locking pressure mechanism 9 is then inserted through opening 18 and rotated until posts 25 fit into notches 20. The posts 25 are positioned on the cylindrical body 21 of the locking pressure mechanism 9 so that the portion of the cylindrical body below posts (i.e. contacting the mount) is sufficient to space the chassis 10 above the surface of the mount 30 so that the surface of flange 13 never touches the polishing surface 41 of the polishing cup 40.

In applications where radioactive specimens are processed, the holding fixture must be handled for cleaning and operations using a remote manipulator. It is therefore preferred to have a plurality of flattened edges 17, 19, around the outer circumference of at least one of the flanges of the chassis 10, and more preferably all of the flanges, to allow for better control in handling the fixture with the manipulator.

It will be apparent to those skilled in the art that many changes and substitutions can be made to the preferred embodiment herein described without departing from the spirit and scope of the present invention as defined by the appended claims.

What is claimed is:

1. A fixture for holding a specimen for polishing comprising:
   (a) an arm;
   (b) a body attached to an end of said arm, said body having a first opening of sufficient dimensions to allow insertion of a specimen for polishing therein and to hold said specimen stable and in place, a second opening axially parallel to said first opening; and
   (c) a pressure means applying pressure against said specimen to hold said specimen in contact with a polishing surface, said pressure means capable of being lockingly engaged within said second opening.

2. A fixture for holding a specimen for polishing in conjunction with a polishing apparatus comprising:
   (a) an arm;
   (b) a body attached to an end of said arm, said body having at least two flanges, said first flange having an opening of sufficient dimensions to allow insertion of a specimen for polishing therein and to hold said specimen stable and in place, a second flange having an opening axially parallel to the opening in said first flange; and
   (c) a pressure means insertable into the opening in said second flange, said pressure means applying pressure against said specimen to hold said specimen in contact with a polishing surface.

3. A fixture according to claim 2, wherein at least one flange has a plurality of flattened edges around the outer circumference of said flange.

4. A fixture according to claim 2, wherein the openings in the flanges are axially aligned.

5. A fixture according to claim 2, constructed from a non-corrosive material.

6. A fixture according to claim 2, wherein:
   (a) said pressure means comprises a cylindrical body, said cylindrical body having one or more posts axially perpendicular thereto, and a fitting attached to one end of said cylindrical body for making connection to the polishing apparatus; and
   (b) said second flange further comprises notches to accommodate said posts to prevent said cylindrical body from rotating.

* * * * *